United States Patent
Kirk et al.

[11] Patent Number: 6,071,853
[45] Date of Patent: Jun. 6, 2000

[54] CRYSTALLINE FLUORAN COMPOUND

[75] Inventors: Roy Alan Kirk, Manchester, United Kingdom; Jonathon Gawtrey, Lyons, France; Michael Heneghan, Manchester, United Kingdom; John Whitworth, Manchester, United Kingdom; Ian Antony Dearden, Manchester, United Kingdom; James Philip Taylor, Macclesfield, United Kingdom; John Barry Henshall, Manchester, United Kingdom

[73] Assignee: Ciba Specialty Chemicals Corporation, Tarrytown, N.Y.

[21] Appl. No.: 09/199,089

[22] Filed: Nov. 24, 1998

[30] Foreign Application Priority Data

Nov. 26, 1997 [GB] United Kingdom .................. 9724871

[51] Int. Cl.⁷ ........................... C07D 311/78; B41M 5/20
[52] U.S. Cl. ........................... 503/221; 549/225; 549/224
[58] Field of Search ........................... 503/221; 549/224, 549/225

[56] References Cited

U.S. PATENT DOCUMENTS

| | | | |
|---|---|---|---|
| 5,283,222 | 2/1994 | Nakatsuka et al. | 503/213 |
| 5,300,473 | 4/1994 | Nakatsuka et al. | 503/221 |
| 5,302,571 | 4/1994 | Otsuji et al. | 503/221 |

FOREIGN PATENT DOCUMENTS

| | | |
|---|---|---|
| 0410206 | 1/1991 | European Pat. Off. . |
| 0435149 | 7/1991 | European Pat. Off. . |
| 0462480 | 12/1991 | European Pat. Off. . |
| 0466040 | 1/1992 | European Pat. Off. . |
| 0477623 | 4/1992 | European Pat. Off. . |
| 0526856 | 2/1993 | European Pat. Off. . |
| 0546577 | 6/1993 | European Pat. Off. . |
| 1357244 | 6/1974 | United Kingdom . |

*Primary Examiner*—Amelia Owens
*Attorney, Agent, or Firm*—Kevin T. Mansfield

[57] ABSTRACT

Disclosed are a novel crystal form of the fluoran compound represented by formula (I) as characterised by specific X-ray powder diffraction pattern and melting range; process for the preparation of said novel crystal form and recording materials comprising the said crystal form.

14 Claims, 2 Drawing Sheets

CRYSTALLINE FLUORAN COMPOUND

TECHNICAL FIELD

The present invention relates to a fluoran compound which is useful as a colour forming compound in recording materials. More particularly, the invention relates to a novel crystal form of the fluoran compound, a process for the preparation of said novel crystal form and to the use of said novel crystal form as a colour former in recording materials such as heat sensitive and pressure sensitive recording materials.

DESCRIPTION OF THE PRIOR ART

Pressure sensitive recording, heat sensitive recording and electroheat sensitive recording have conventionally been used as systems for recording transferred information through the mediation of external energy, such as pressure, heat or electricity, by utilising a colour reaction between a colourless or pale coloured electron donative compound (colour forming compound) and an organic or inorganic electron acceptor (developer).

In such recording systems, many fluoran compounds have been widely used as the colour forming compound. For example, 3-dimethylamino-6-methyl-7-anilinofluoran compound (formula 1) has been disclosed in GB 1,357,244. There is no mention in GB 1,357,244 of the crystal structure of the fluoran obtained. The fluoran compound represented by formula (I) has been disclosed in GB 1,357,244 as a colour forming material having a melting point in the range 201–201.5° C.

Formula I

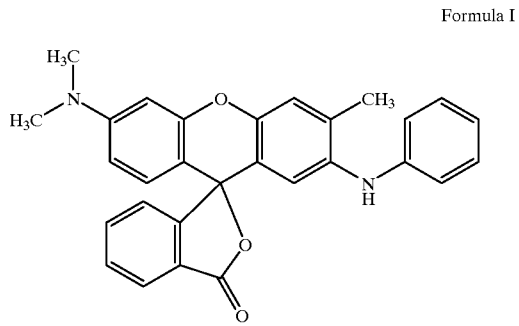

When compound of Formula (I), as obtained by the process of GB 1,357,244, is used as a colour developing material for recording materials, such as a heat sensitive recording material, and mixed with a developer such as Bisphenol A, the compound itself colours grey and provides only a grey (soiled) paper on applying the compound to paper, before application of any external heat source. Further the compound obtained by the process of the art has a disadvantage of poor storage stability such as light resistance which can lead to difficulties in practical use.

OBJECT OF THE INVENTION

An object of the present invention is to overcome the undesirable properties of the fluoran compound of formula (I) as a colour forming agent of the recording materials. Thus the present invention provides a novel crystalline form of fluoran compound (I) having excellent properties for use in the pressure sensitive and heat sensitive recording material, particularly in the heat sensitive recording materials.

DETAILED DESCRIPTION OF THE INVENTION

Figure 1:
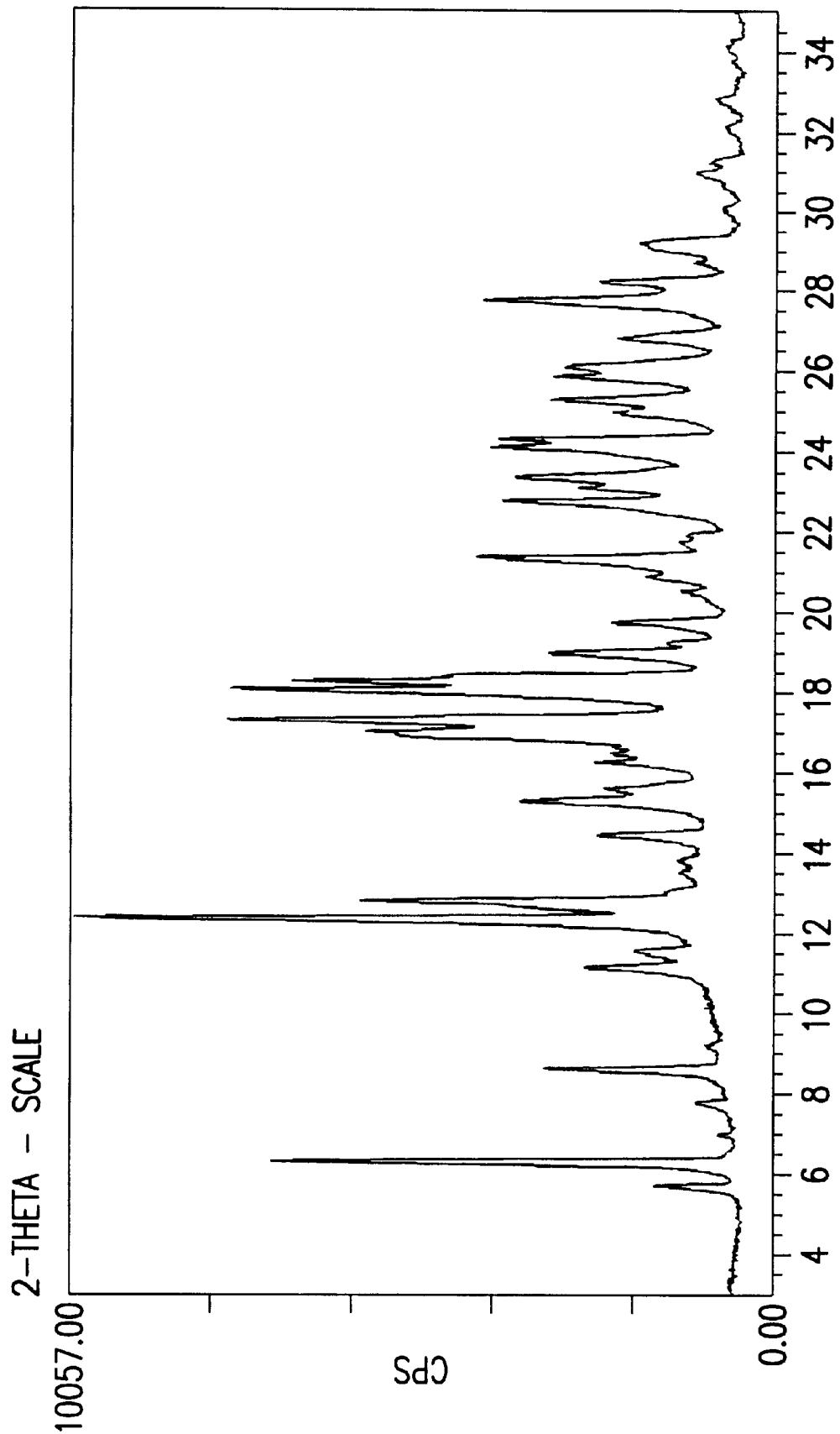
FIG. 1 is an X-ray powder diffraction diagram of a novel crystal form of the fluoran compound of formula (I) which was prepared and isolated according to the process of the present invention as illustrated in Examples 1–3.

The fluoran compound represented by the formula (I) can be prepared by reacting a keto acid of formula (II) with a diphenylamine of formula (III):

Formula II

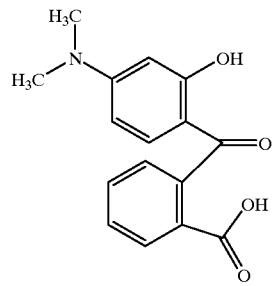

Formula III

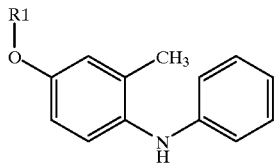

wherein R1 is Hydrogen or a lower alkyl group having 1–4 C atoms, in the presence of a dehydrating condensation agent, for example, concentrated sulphuric acid, oleum-concentrated sulphuric acid mixtures, polyphosphoric acid, phosphorous pentaoxide or anhydrous aluminium chloride, and mixtures thereof, preferably concentrated sulphuric acid or oleum-concentrated sulphuric acid mixtures, and thereafter bringing the reaction mixture to an alkaline pH in the presence of organic solvent. The solvent used is not specifically limited provided that it is insoluble or only slightly soluble in water. Thus, the solvent may be exemplified by aromatic hydrocarbons such as benzene, toluene, xylenes or trimethyl benzenes, halogenated aromatic hydrocarbons such as chlorobenzene, dichlorobenzenes, trichlorobenzenes or bromonapthalenes, halogenated aliphatic hydrocarbons such as dichloroethane or tetrachloroethane, aliphatic hydrocarbons such as hexane, heptane, octane or n-decane and alicyclic hydrocarbons such as cyclohexane or methylcyclohexane. In addition to the above there may also be used alcohols such as amyl alcohol, 2-ethylhexanol or octyl alcohol, ethers such as isopropyl ether, or ketones such as cyclohexanone. The solvent may be used singly or as a mixture.

The condensation reaction is generally carried out at from 0 to about 100° C. preferably from about 10 to about 60° C. for several to 100 hours. When the reaction is carried out in concentrated sulphuric acid or oleum-concentrated sulphuric acid mixtures, the reaction temperature is preferably in the range from 0 to about 50° C. The reaction time depends upon the selected reaction temperature and hence the reaction is conducted for a sufficient time to permit the reaction to go to completion. Completion of reaction is determined using standard analytical techniques, including but not limited to, thin layer chromatography, gas chromatography and liquid chromatography.

After the dehydrating condensation reaction is completed the alkali treatment may be carried out by addition of the reaction mass to a stirred mixture of base, water and organic solvent. Suitable bases include, for example, potassium hydroxide, lithium hydroxide, sodium hydroxide, potassium carbonate, sodium carbonate, lithium carbonate, ammonia or organic bases such as triethylamine and mixtures thereof. The preferred bases for use in the process of the present invention are sodium hydroxide and potassium hydroxide. Suitable solvents include toluene, xylene, halogenated aromatic solvents such as chlorobenzene, esters, ketones, alcohols such as 2-ethylhexanol and mixtures thereof. Additional base may be added as required to achieve an alkalinity within the pH range of 9–12. The treatment may be conducted in a temperature of from 0° C. to the boiling point of the solvent or solvent mixture in use, preferably 50–100° C. During this process the novel crystalline product according to the present invention precipitates from the reaction media. The crystalline precipitate may be isolated by filtration from the reaction liquors.

After isolation, the crystal may be washed as desired with water and/or an organic solvent. The solvent may be exemplified by aromatic hydrocarbons such as benzene, toluene, xylenes or trimethyl benzenes, halogenated aromatic hydrocarbons such as chlorobenzene, dichlorobenzenes, trichlorobenzenes or bromonapthalenes, halogenated aliphatic hydrocarbons such as dichloroethane or tetrachloroethane, aliphatic hydrocarbons such as hexane, heptane, octane or n-decane and alicyclic hydrocarbons such as cyclohexane or methylcyclohexane. In addition to the above there may also be used alcohols such as methanol, ethanol, isopropanol, butanol, amyl alcohol, 2-ethylhexanol or octyl alcohol, ethers such as isopropyl ether, or ketones such as cyclohexanone. The solvent may be used singly or as a mixture.

Alternatively, after the dehydrating condensation, the reaction mass may be quenched into a stirred water-solvent mixture at from 0 to about 100° C., preferably 60–90° C. The solvent used is not specifically limited provided that it is insoluble or only slightly soluble in water. Thus, the solvent may be exemplified by aromatic hydrocarbons such as benzene, toluene, xylenes or trimethyl benzenes, halogenated aromatic hydrocarbons such as chlorobenzene, dichlorobenzenes, trichlorobenzenes or bromonapthalenes, halogenated aliphatic hydrocarbons such as dichloroethane or tetrachloroethane, aliphatic hydrocarbons such as hexane, heptane, octane or n-decane and alicyclic hydrocarbons such as cyclohexane or methylcyclohexane. In addition to the above there may also be used alcohols such as amyl alcohol, 2-ethylhexanol or octyl alcohol, ethers such as isopropyl ether, or ketones such as cyclohexanone. The solvent may be used singly or as a mixture. Sufficient base, for example potassium hydroxide, lithium hydroxide, sodium hydroxide, potassium carbonate, sodium carbonate, lithium carbonate, ammonia or organic bases such as triethylamine and mixtures thereof, is then added to provide an organic-aqueous phase separation. The aqueous layer may then be separated if desired. To the organic phase or biphasic mixture, containing the phthalide intermediate, is then added further base, as above, to pH>10. The reaction mass is stirred at from 0 to about 100° C., preferably 60–90° C., in order to complete cyclisation to the fluoran product. The reaction mass is then adjusted to 25° C. and the precipitated crystalline product may then be isolated by filtration as discussed above. The reaction product is isolated by filtration from the reaction liquors as the crystal of the invention. After isolation, the crystal may be washed with water and/or an organic solvent as defined previously. In this manner is isolated the novel crystalline fluoran of the invention.

Further, the novel crystal form of the fluoran of the present invention can be prepared from the prior art low melting point compound of formula (I). The low melting fluoran, as obtained by the process of GB 1,357,244, is stirred at from 0 to about 100° C., preferably 60–90° C., in an organic solvent, suitable solvents include toluene, xylene, halogenated aromatic solvents such as chlorobenzene, alcohols such as 2-ethylhexanol, preferably toluene. The mixture is then treated with aqueous base, for example potassium hydroxide, lithium hydroxide, sodium hydroxide, potassium carbonate, sodium carbonate, lithium, carbonate, ammonia or organic bases such as triethylamine and mixtures thereof. The organic layer is then separated and the temperature adjusted to 25° C. and the precipitated product is then isolated by filtration. The precipitated reaction product is isolated by filtration from the reaction liquors. After isolation, the crystal may be washed with water, an organic solvent, for example, the above solvent or an aliphatic alcohol such as methanol, ethanol, iso-propanol or n-butanol. In this manner is isolated the novel crystalline fluoran material according to the present invention having a melting point in the range of 205–208° C.

If desired, the crystalline product, suitably isolated by any of the aforementioned methods, may be further purified by precipitation from an organic solvent or from a organic solvent-water mixture, for example, toluene, benzene, xylene, methanol, ethanol, iso-propanol, n-butanol, acetonitrile, dimethylformamide or mixtures of these solvents. The crystal may be dissolved by heating to a temperature range of from room temperature to the boiling point of the chosen solvent, or above it under pressure in an autoclave. After complete dissolution the crystal may be precipitated with stirring or on standing.

This recrystallised crystalline product may then be dried by a usual method, such as at a raised temperature, below the melting point of the crystal of the invention, under vacuum, to obtain the novel crystalline form of fluoran compound (I) of the present invention.

Some fluoran compounds have been known to have different crystalline forms, that is so called crystal modifications as described in for example, EP435149, EP526856, EP546577.

The term 'novel crystalline form of the fluoran compound of the formula (I) of the invention' includes crystal modifications which can exist in the fluoran compound of formula (I) of the invention.

The crystalline fluoran compound, suitably isolated by any of the aforementioned methods, according to the present invention exhibits in the X-ray powder diffraction pattern high peaks at the diffraction angle ($2\theta$) of 6.31, 12.37, 12.83, 17.02, 17.33, 18.10, 18.30 as illustrated in FIG. 1. The thus characterised crystal structure (or form) of the fluoran compound as isolated by the method according to the present invention is a novel crystal form of the fluoran of formula (I). The chemical structure of the fluoran of formula (I) as isolated by the method according to the present invention was confirmed using standard analytical techniques including proton nuclear magnetic resonance spectroscopy and time of flight mass spectroscopy.

Figure 2:
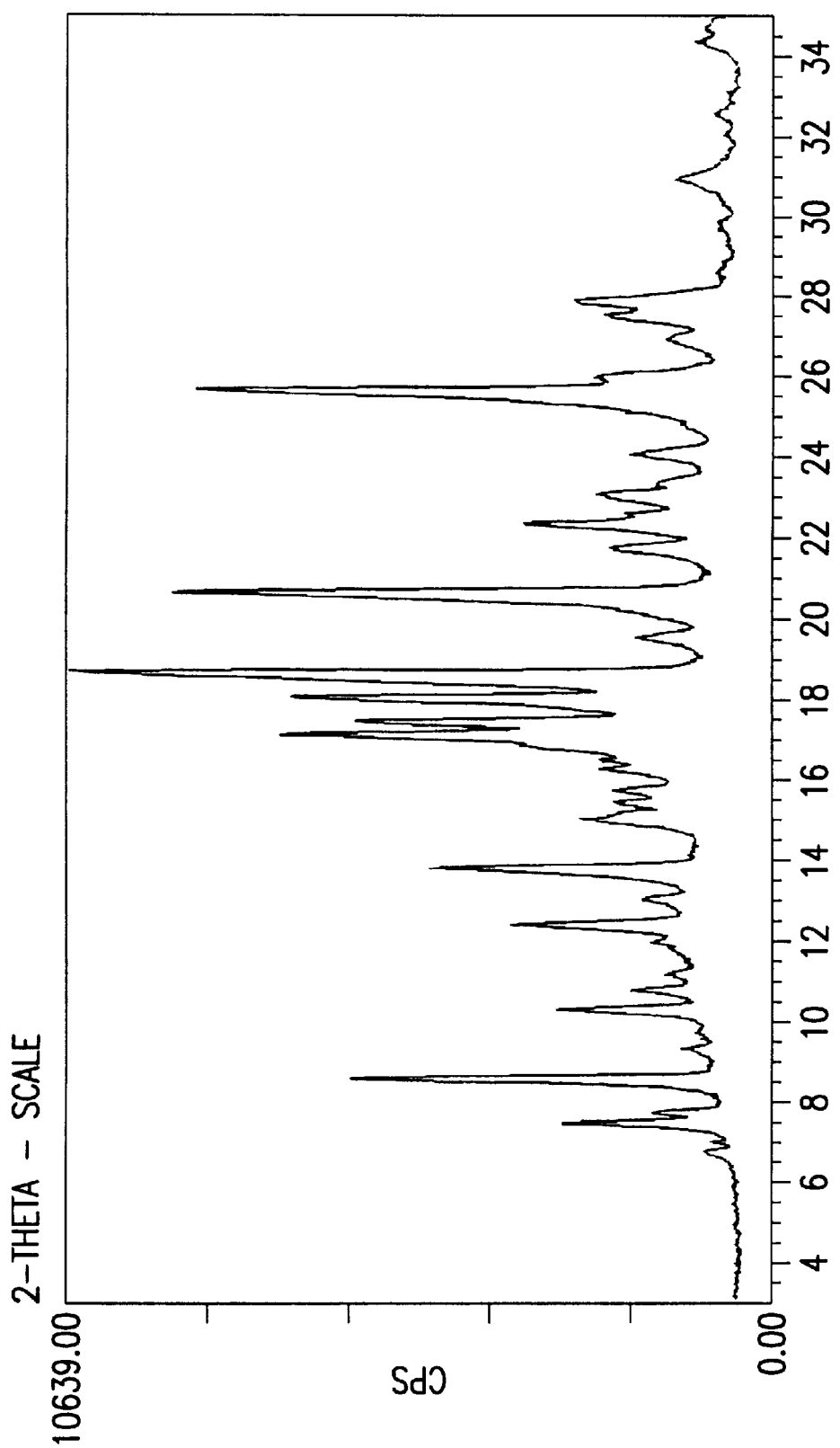
FIG. 2 is an X-ray powder diffraction diagram of a crystal form of the fluoran compound of formula (I) which was prepared and isolated according to the process of GB 1,357,244 as illustrated by Comparative Example 1. In each case the axis of abscissa indicates an angle of diffraction (2θ) and the axis of ordinate indicates strength of diffraction.

The compound of the formula (I) isolated by the method disclosed in GB1357244 exhibits in the X-ray powder diffraction pattern high peaks at the diffraction angle (2θ) of 8.53, 17.11, 17.43, 18.02, 18.61, 20.63, 25.63 as illustrated in FIG. 2.

The melting point of the novel crystal form of the fluoran according to the present invention is distinct from the melting point of the previously known fluoran crystal form.

The novel crystal form of the fluoran compound of the present invention has a melting point of 205–208° C. as measured on an Electrothermal Melting Point Apparatus Model 9200. The melting point of the fluoran of formula (I) disclosed in GB 1357244 was cited to be 201–201.5° C., in our hands 201–203° C.

The novel crystal form of the fluoran compound of the formula (I), as isolated by any of the processes according to the present invention, may be used as a colour forming compound for various recording materials. Isolated material, as defined herein, means both crystalline material as obtained from precipitate and filtration as well as material which has been further purified, by say, recrystallisation.

As such it is a further object of the present invention to provide recording material comprising the novel crystalline form of the fluoran of formula (I) according to the present invention. The recording materials of the present invention include pressure sensitive recording material and heat sensitive recording material. The novel crystalline form of the fluoran according to the present invention is particularly suitable for heat sensitive recording materials.

In such case, the fluoran compound can be used singly or as a mixture with other colour forming compounds such as triphenylmethanes, lactones, fluorans, benzoxazines and spiropyrans in order to adjust the developed hue if desired. The novel crystalline fluoran compound of the invention may also be used together with further black colour formers to improve the thermal sensitivity and image stability of the recording material. Other colour formers which may be used as above, include but are not limited to; 3-diethylamino-6-methylfluoran, 3-diethylamino-6-methyl-7-anilinofluoran, 3-diethylamino-6-methyl-7-(2,4-dimethylanilino) fluoran, 3-diethylamino-6-methyl-7-chlorofluoran, 3-diethylamino-6-methyl-7-(3-trifluoromethylanilino) fluoran, 3-diethylamino-6-methyl-7-(2-chloroanilino) fluoran, 3-diethylamino-6-methyl-7-(4-chloroanilino) fluoran, 3-diethylamino-6-methyl-7-(2-fluoroanilino) fluoran, 3-diethylamino-6-methyl-7-(4-n-octylanilino) fluoran, 3-diethylamino-6-methyl-7-(4-dibenzylamino) fluoran, 3-diethylamino-6-chloro-7-methylfluoran, 3-diethylamino-6-chloro-7-anilinofluoran, 3-diethylamino-6-methyl-7-(4-methylanilino) fluoran, 3-diethylamino-6-ethoxyethyl-7-anilinofluoran, 3-diethylamino-7-methylfluoran, 3-diethylamino-7-chlorofluoran, 3-diethylamino-7-(3-trifluoromethylanilino) fluoran, 3-diethylamino-7-(2-chloroanilino) fluoran, 3-diethylamino-7-(2-fluoroanilino) fluoran, 3-diethylamino-benzo[a]fluoran, 3-diethylamino-benzo[c]fluoran, 3-dibutylamino-6-methyl fluoran, 3-dibutylamino-6-methyl-7-anilinofluoran, 3-dibutylamino-6-methyl-7-(2,4-dimethylanilino) fluoran, 3-dibutylamino-6-methyl-7-(2-chloroanilino) fluoran, 3-dibutylamino-6-methyl-7-(4-chloroanilino) fluoran, 3-dibutylamino-6-methyl-7-(2-fluoroanilino) fluoran, 3-dibutylamino-6-methyl-7-(3-trifluoromethylanilino) fluoran, 3-dibutylamino-6-ethoxyethyl-7-anilinofluoran, 3-dibutylamino-6-chloro-anilinofluoran, 3-dibutylamino-6-methyl-7-(4-methylanilino) fluoran, 3-dibutylamino-7-(2-chloroanilino) fluoran, 3-dibutylamino-7-(2-fluoroanilino) fluoran, 3-dipentylamino-6-methyl-7-anilinofluoran, 3-dipentylamino-6-methyl-7-(4-2-chloroanilino) fluoran, 3-dipentylamino-7-(3-trifluoromethylanilino) fluoran, 3-dipentylamino-6-chloro-7-anilinofluoran, 3-dipentylamino-7-(4-chloroanilino) fluoran, 3-pyrrolidino-6-methyl-7-anilinofluoran, 3-piperidino-6-methyl-7-anilinofluoran, 3-(N-methyl-N-propylamino)-6-methyl-7-anilinofluoran, 3-(N-methyl-N-cyclohexylamino)-6-methyl-7-anilinofluoran, 3-(N-ethyl-N-cyclohexylamino)-6-methyl-7-anilinofluoran, 3-(N-ethyl-p-toluidino)-6-methyl-7-anilinofluoran, 3-(N-ethyl-N-isoamylamino)-6-methyl-7-anilinofluoran, 3-(N-ethyl-N-isoamylamino)-6-chloro-7-anilinofluoran, 3-(N-ethyl-N-tetrahydrofurfurylamino)-6-methyl-7-anilinofluoran, 3-(N-ethyl-N-isobutylamino)-6-methyl-7-anilinofluoran, 3-(N-ethyl-N-ethoxypropylamino)-6-methyl-7-anilinofluoran, 3-cyclohexylamino-6-chlorofluoran, 2-methyl-6-p-(p-dimethylaminophenyl)aminoanilinofluoran, 2-methoxy-6-p-(p-dimethylaminophenyl)aminoanilinofluoran, 2-chloro-3-methyl-6-p-(p-phenylaminophenyl)aminoanilinofluoran, 2-diethylamino-6-p-(p-dimethylaminophenyl)aminoanilinofluoran, 2-phenyl-6-methyl-6-p-(p-phenylaminophenyl)aminoanilinofluoran, 2-benzyl-6-p-(p-phenylaminophenyl)aminoanilinofluoran, 3-methyl-6-p-(p-dimethylaminophenyl)aminoanilinofluoran, 3-diethylamino-6-p-(p-diethylaminophenyl)aminoanilinofluoran, 3-diethylamino-6-p-(p-dibutylaminophenyl)aminoanilinofluoran, 2,4-dimethyl-6-[(4-dimethylamino)anilino]fluoran, 3,6,6'-tris(dimethylamino)spiro[fluorene-9,3'-phthalide], 3,6,6'-tris(diethylamino)spiro[fluorene-9,3'-phthalide], 3,3-bis(p-dimethylaminophenyl)-6-dimethylaminophthalide, 3,3-bis(p-dimethylaminophenyl)phthalide, 3,3-bis-[2-(p-dimethylaminophenyl)-2-(p-methoxyphenyl)ethenyl-4,5,6,7-tetrabromophthalide, 3,3-bis-[2-(p-dimethylaminophenyl)-2-(p-methoxyphenyl)ethenyl-4,5,6,7-tetrachlorophthalide, 3,3-bis[1,1-bis(4-pyrrolidinophenyl)ethylene-2-yl]-4,5,6,7-tetrabromophthalide, 3,3-bis-[1-(4-methoxyphenyl)-1-(4-pyrridinophenyl)ethylene-2-yl]-4,5,6,7-tetrachlorophthalide, 3-(4-diethylamino-2-ethoxyphenyl)-3-(1-ethyl-2-methylindole-3-yl)-4-azaphthalide, 3-(4-diethylamino-2-ethoxyphenyl)-3-(1-octyl-2-methylindole-3-yl)-4-azaphthalide, 3-(4-cyclohexylethylamino-2-methoxyphenyl)-3-(1-ethyl-2-methylindole-3-yl)-4-azaphthalide, 3,3-bis(1-ethyl-2-methylindole-3-yl) phthalide and mixtures thereof.

When preparing a heat sensitive recording material of the invention, the novel crystal form of the fluoran compound of the formula (I) of the present invention and a developer are pulverised separately in water or suitable solvent to form an aqueous or other dispersion. Optionally, a fine dispersion of sensitiser may be included. The fine particle dispersions thus obtained are combined and then mixed With conventional amounts of binder, filler and lubricant.

Representative examples of the developer which are suitable for use in the heat sensitive recording material include but are not limited to: substituted phenols and bisphenols such as 4,4'-isopropylidene Bisphenol, 4,4'-sec-butylidene bisphenol, 4,4'-cyclohexylidene Bisphenol, 2,2-bis-(4-hydroxyphenyl)-4-methylpentane, 2,2-dimethyl-3,3-di(4-hydroxyphenyl)butane, 2,2'-dihydroxydiphenyl, 1-phenyl-1,1-bis(4-hydroxyphenyl)butane, 4-phenyl-2,2-bis(4-hydroxyphenyl)butane, 1-phenyl-2,2-bis(4-hydroxyphenyl)butane, 2,2-bis(4'-hydroxy-3'-methylphenyl)-4-methylpentane, 2,2-bis(4'-hydroxy-3'-tert-butyllphenyl)-4-methylpentane, 4,4'-sec-butylidene-bis(2-methylphenol), 4,4'-isopropylidene-bis(2-tert-butylphenol), 2,2-bis(4'-hydroxy-3'-isopropylphenyl)-4-methylpentane, allyl-4,4-bis(4'-hydroxyphenyl) pentanoate, propargyl- 4,4-bis(4'-hydroxyphenyl) pentanoate, n-propyl-4,4-bis (4'- hydroxyphenyl) pentanoate, 2,4-bis(phenylsulfonyl) phenol, 2-(4-methylsulfonyl)-4-(phenylsulfonyl) phenol, 2-(phenylsulfonyl)-4-(4-methylsulfonyl) phenol, 2,4-bis(4-methylphenylsulfonyl) phenol, pentamethylene-bis(4-hydroxybenzoate), 2,2-dimethyl-3,3-di(4-hydroxyphenyl) pentane, 2,2-di(4-hydroxyphenyl)hexane; sulphur containing bisphenols such as; 4,4'-dihydroxydiphenyl thioether, 1,7-di(4-hydroxyphenylthio)-3,5-dioxaheptane, 2,2'-bis(4-hydroxyphenylthio)diethyl ether, 4,4'-dihydroxy-3,3'-dimethylphenyl thioether; hydroxybenzoate esters such as; benzyl-4-hydroxybenzoate, ethyl-4-hydroxybenzoate, propyl-4-hydroxybenzoate, isopropyl-4-hydroxybenzoate, butyl-4-hydroxybenzoate, isobutyl-4-hydroxybenzoate; hydroxy sulfones such as; 4,4'-dihydroxydiphenyl sulfone, 2,4'-dihydroxydiphenyl sulfone, 4-hydroxy-4'-methyldiphenyl sulfone, 4-hydroxy-4'-isopropoxydiphenyl sulfone, 4-hydroxy-4'-butoxydiphenyl sulfone, 4,4'-dihydroxy-3,3'-diallyldiphenyl sulfone, 3,4-dihydroxy-4'-methyldiphenyl sulfone, 4,4'-dihydroxy-3,3',5,5'-tetrabromodiphenyl sulfone; sulphonyl ureas such as 4,4'-bis(p-toluenesulphonylaminocarbonylamino) diphenylmethane; diesters of 4-hydroxyphthalic acid such as; dimethyl 4-hydroxyphthalate, dicyclohexyl 4-hydroxyphthalate, diphenyl 4-hydroxyphthalate; salicylic acid derivatives such as; 4-[2-(4-methoxyphenyloxy) ethyloxy]salicylate, 3,5-di-tert-butylsalicylic acid, 3-benzyl salicylic acid, 3-(α-methylbenzyl) salicylic acid, 3-phenyl-5-(α,α-dimethylbenzyl) salicylic acid, 3,5-di-α-methylbenzyl salicylic acid; metal salts of salicylic acid such as zinc salicylate; benzoic acid derivatives such as; 2-benzylsulfonylbenzoic acid, 3-cyclohexyl-4-hydroxybenzoic acid; metal salts of benzoic acid such as; zinc benzoate, zinc 4-nitrobenzoate. resorcylic anilide derivatives as described in U.S. Pat. No. 5,607,894 and included herein by reference; phthalic acid and isophthalic acid derivatives such as; 4-(4'-phenoxybutoxy)phthalic acid, 4-(2'-phenoxyethoxy)phthalic acid, 4-(3'-phenylpropyloxy) phthalic acid, mono(2-hydroxyethyl)-5-nitro-isophthalic acid, 5-benzyloxycarbonyl isophthalic acid, 5-(1'-phenylethanesulfonyl) isophthalic acid and mixtures thereof.

Representative binders used for the heat sensitive recording material includes, but are not limited to; polyvinyl alcohol (fully and partially hydrolysed), carboxy, amide, sulfonic and butyral modified polyvinyl alcohols, derivatives of cellulose such as hydroxyethyl cellulose, methyl cellulose, ethyl cellulose, carboxymethyl cellulose and acetyl cellulose, copolymer of styrene-maleic anhydride, copolymer of styrene-butadiene, polyvinyl chloride, polyvinyl acetate, polyacrylamide, polyamide resin and mixtures thereof.

Exemplary fillers which can be used include, but are not limited to; calcium carbonate, kaolin, calcined kaolin, aluminium hydroxide, talc, titanium dioxide, zinc oxide, silica, polystyrene resin, urea-formaldehyde resin, hollow plastic pigment and mixtures thereof.

Representative lubricants for use in heat sensitive recording materials include, but are not limited to; dispersions or emulsions of stearic acid, polyethylene, carnauba wax, paraffin wax, zinc stearate or calcium stearate and mixtures thereof.

Other additives can also be employed, if necessary. Exemplary additives include sensitisers, stabilisers and the like.

Representative sensitisers for use in heat sensitive recording materials include but are not limited to; stearamide, methylol stearamide, p-benzylbiphenyl m-terphenyl, 2-benzyloxynaphthalene, dibenzyl oxalate, di(4-methylbenzyl) oxalate, di(4-chlorobenzyl) oxalate, dimethyl phthalate, dibenzyl terephthalate, dibenzyl isophthalate, 1,2-diphenoxyethane, 1,2-bis(4-methylphenoxy) ethane, 1,2-bis (3-methylphenoxy) ethane, 4,4'-dimethylbiphenyl, phenyl-1-hydroxy-2-naphthoate, 4-methylphenyl biphenyl ether, 2,2-bis(3,4-dimethylphenyl) ethane, 2,3,5,6-4'-methyldiphenyl methane, 1,4-diethoxynaphthalene, o-xylylene-bis(phenyl ether), 4-(m-methylphenoxymethyl) biphenyl, p-hydroxyacetanilide, p-hydroxybutyranilide, p-hydroxynonananilide, p-hydroxylauranilide, p-hydroxyoctadecananilide and mixtures thereof.

Representative stabilisers for use in heat sensitive recording materials include but are not limited by; 2,2'-methylene-bis(4-methyl-6-tert-butylphenol), 2,2'-methylene-bis(4-ethyl-6-tert-butylphenol), 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl) butane, 1,1,3-tris(2-methyl-4-hydroxy-5-cyclohexylphenyl) butane, bis(3-tert-butyl-4-hydroxy-6-methylphenyl) sulfone, bis(3,5-dibromo-4-hydroxyphenyl) sulfone, 4,4'-sulfinyl bis(2-tert-butyl-5-methylphenol), 2,2'-methylene bis(4,6-di-tert-butylphenyl) phosphate and alkali metal, ammonium and polyvalent metal salts thereof, 4-benzyloxy-4'-(2-methylglycidyloxy) diphenyl sulfone, 4,4'-diglycidyloxydiphenyl sulfone, 1,4-diglycidyloxybenzene, 4-[α-(hydroxymethyl)benzyloxy]-4-hydroxydiphenyl sulfone, metal salts of p-nitrobenzoic acid, metal salts of phthalic acid mono benzyl ester, metal salts of cinnamic acid and mixtures thereof.

The coating liquid obtained by the addition of additives to the particle dispersion of fluoran and developer can be applied to a suitable substrate such as paper, plastic sheet and resin coated paper, and used as the heat sensitive recording material. The system of the invention can be employed for other end use applications using colour forming materials, for example, a temperature indicating material.

The heat sensitive recording material prepared by using the novel crystal form of the fluoran of the present invention has excellent background whiteness, lightfastness, moisture and heat resistance properties as compared with the recording material obtained by using the compound of the formula (I) which is prepared by the process disclosed in GB 1357244 and having a melting point of 201–201.5° C. For example, when bisphenol A is used as a developer, the heat sensitive recording paper obtained by a process of the invention demonstrates excellent background whiteness (brightness) of paper after application of the coating liquid and in storage stability, i.e. resistance to light, heat and moisture, of uncoloured portion of the coated paper, as illustrated in table 1.

The heat sensitive recording material prepared by using the novel crystal form of the fluoran of the present invention has excellent background whiteness, lightfastness, moisture and heat resistance properties as compared with conventionally used compounds of formula (IV) Yamada Black S-205, or the compound of formula (V) Pergascript Black T-R illustrated hereinafter. For example, when bisphenol A is used as a developer, the heat sensitive recording paper obtained by a process of the invention demonstrates excellent background whiteness (brightness) of paper after application of the coating liquid and in storage stability, i.e. resistance to light, heat and moisture, of uncoloured portion of the coated paper, as illustrated in table 1.

Formula (IV)

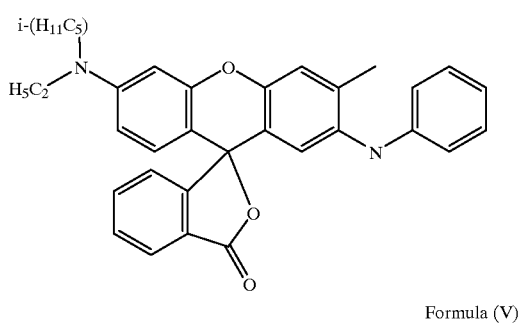

Formula (V)

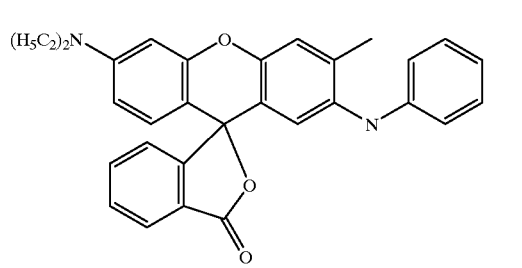

TABLE 1

| Coating Formulation on heat sensitive paper | Background Whiteness (Brightness) | | |
|---|---|---|---|
| | Immediately after application | Light Resistance | Moisture and Heat Resistance |
| Crystal of Invention (Example 4) | O | O | O |
| Fluoran compound of melting point 201–201.5°C. (Comparative Example 2) | X | X | X |
| Compound of formula (IV) (Comparative Example 3) | X | X | X |
| Compound of formula (V) (Comparative Example 4) | X | X | X |
| 1:1 ratio of crystal of invention and Pergascript Black T-2R (Example 5) | X | O | O |
| 1:1 ratio of crystal of invention and Yamada black S-205 (Example 6) | X | X | O |

Results were evaluated by visual observation.

Evaluation at immediately after application was conducted by observing the brightness of the paper.

O—high brightness
X—Soiled to grey

Evaluation of light resistance was conducted by inspecting the degree of yellowing of the uncoloured portion of the paper after exposure to 120 hours of artificial daylight.

O—Virtually no yellowing and high brightness maintained.

X—significant yellowing or discolouration to brown

Evaluation of heat and moisture resistance was conducted by examining the soiling of the uncoloured portion of paper after storage at 60° C. and 50% relative humidity for one hour.

O—virtually no soiling and high brightness maintained
X—Significant soiling to grey.

EXAMPLE 1

Preparation of Novel Crystalline Form of Fluoran having Formula (I)

To 185 g of 98% sulphuric acid was added 46 g of 2'-carboxy-4-dimethylamino-2-hydroxybenzophenone over 1 hr with the temperature being maintained below about 30° C. Once in solution, 34.4 g of 4-methoxy-2-methyldiphenylamine was added and the mixture was stirred for 7 hr at 30° C. The reaction mass was then added over about 1 hr to a mixture of 200 g toluene-300 g water-30 g 100° TW sodium hydroxide. During the addition the mass was kept alkaline by portionwise addition of a further 320 g 100° TW sodium hydroxide. The precipitated crystalline product was isolated by filtration and washed with water and methanol to yield 61 g of 3dimethylamino-6-methyl-7-anilinofluoran as a white powder having a melting point 205–208° C. as measured on an Electrothermal Melting Point apparatus Model 9200.

EXAMPLE 2

Preparation of Novel Crystalline Form of Fluoran having Formula (I)

To 42.2 g of 98% sulphuric acid and 10.5 g oleum was added 11.4 g of 2'-carboxy-4-dimethylamino-2-hydroxybenzophenone over about 2 hr with the temperature being maintained below about 25° C. by use of an ice-bath. Once in solution, 8.5 g of 4-methoxy-2-methyldiphenylamine was added and the mixture was stirred for about 3 hr at 30° C. The reaction mass was then added, over about 30 minutes with stirring, to a mixture of 90 g toluene-100 g water at 85° C. To this was then added, over 30 minutes, 13.5 g sodium hydroxide 100° TW and 13.5 g water. Agitation was ceased and the separated aqueous phase was removed. To the remaining organic phase was added 35 g sodium hydroxide 100° TW and 100 g water and the reaction was stirred for 2 h at 85° C. The reaction was cooled to 25° C. and the precipitated product was isolated by filtration. The product was washed with hot water (about 60° C.) then methanol and dried to yield 13.3 g of 3-dimethylamino-6-methyl-7-anilinofluoran as a white powder having a melting point 207.5–208° C.

COMPARATIVE EXAMPLE 1

Preparation of Fluoran Compound of Formula 1 by the Process Disclosed in GB 1,357,244

To 55.2 g of 98% sulphuric acid was added 5.7 g of 2'-carboxy-4-dimethylamino-2-hydroxybenzophenone over 1 hr with the temperature being maintained below 30° C. Once in solution, 4.3 g of 4-methoxy-2-methyldiphenylamine was added and the mixture was stirred for 70 hr at 20–25° C. The reaction mass was then added slowly to 200 g water at 60° C. and the mixture was then adjusted to pH=10 by addition of 90 g 100° TW sodium hydroxide. The reaction was stirred for 2 hr at 80° C. The resulting black precipitate was isolated by filtration and recrystallised from toluene to give 5.7 g of the fluoran of formula (I) as a beige powder, melting point 201–203° C.

EXAMPLE 3

Conversion of compound of formula 1 prepared by the process disclosed in GB 1,357,244 to the novel crystal form of the fluoran of the invention.

The fluoran prepared in comparative example 1, 3 g, was stirred with 50 ml toluene, 50 ml water and 5 g 100° TW sodium hydroxide at 80–90° C. for about 30 minutes. The mixture was allowed to settle. The organic layer was separated and allowed to cool to room temperature. The precipitated product was isolated by filtration from the organic layer. The product was washed with toluene then water and dried to yield 2.2 g of 3-dimethylamino-6-methyl-7-anilinofluoran as a white powder having a melting point 206–208° C.

EXAMPLE 4

Preparation of heat sensitive coating formulations comprising the novel crystalline form of Fluoran having formula (I).

Dispersions A–C were prepared by grinding the compositions shown below in an attritor until an average particle size of 1–1.5μ was attained.

| Dispersion A (Colour Former) | |
|---|---|
| Novel Crystal Form of Example 1 | 3.01 parts |
| Polyvinyl alcohol (10% aq. soln.) | 10.50 parts |
| Water | 6.49 parts |
| Dispersion B (Colour Developer) | |
| Bis Phenol A | 7.5 parts |
| Polyvinyl alcohol (10% aq. soln.) | 7.5 parts |
| Water | 22.5 parts |
| Dispersion C (Sensitiser) | |
| p-Benzylbiphenyl | 10.0 parts |
| Polyvinyl alcohol (10% aq. soln.) | 10.0 parts |
| Water | 20.0 parts |

A thermal coating mixture was then prepared by combining together the following components

| | parts by weight |
|---|---|
| Dispersion A | 6.6 |
| Dispersion B | 10.0 |
| Dispersion C | 6.0 |
| Calcium Carbonate (25% aq. dispersion) | 12.0 |
| Zinc stearate (33% aq. dispersion) | 0.9 |
| Polyvinyl alcohol (10% aq. soln.) | 4.5 |
| Tinopal ® ABP-X (fluorescent whitening agent) | 0.12 |
| Water | 2.48 |

This coating mixture was applied on one side of a base paper weighing 50 g/m2 in a coating weight of about 5.0 g/m2 and then dried. The resulting sheet was calendered by means of a laboratory calender to produce a recording sheet with excellent background whiteness.

The heat sensitive paper rapidly developed a black colour by heating. After exposing the heat sensitive recording paper to 120 hrs of artificial daylight the uncoloured portion showed virtually no soiling and retained high brightness. After storing at 60° C. and 50% relative humidity for 1 hr the uncoloured portion showed virtually no soiling and retained high brightness.

COMPARATIVE EXAMPLE 2

Preparation of heat sensitive recording paper by using the crystal of the fluoran compound of formula (I) obtained in Comparative Example 1

A heat sensitive recording paper was prepared by the process described in Example 4, except the novel crystal form isolated in Example 1 was replaced by the known fluoran as disclosed in GB 1,357,244 and as isolated in Comparative Example 1. After calendering the heat sensitive recording paper showed a degree of soil to grey.

The heat sensitive paper rapidly developed a black colour by heating. After exposing the heat sensitive recording paper to 120 hrs of artificial daylight the uncoloured portion showed a high degree of soil to yellow. After storing at 60° C. and 50% relative humidity for 1 hr the uncoloured portion showed a high degree of soil to grey.

COMPARATIVE EXAMPLE 3

Preparation of heat sensitive recording paper by using the crystal of the fluoran compound of formula (IV)

A heat sensitive recording paper was prepared by the process described in Example 4 except the novel crystal form of fluoran (I) as isolated in Example 1 was replaced by the fluoran compound of formula (IV). After calendering the heat sensitive recording paper showed a degree of soil to grey.

The heat sensitive paper rapidly developed a black colour by heating. After exposing the heat sensitive recording paper to 120 hrs of artificial daylight the uncoloured portion showed a high degree of soil to yellow. After storing at 60° C. and 50% relative humidity for 1 hr the uncoloured portion showed a high degree of soil to grey.

COMPARATIVE EXAMPLE 4

Preparation of heat sensitive recording paper by using the crystal of the fluoran compound of formula (V).

A heat sensitive recording paper was prepared by the process described in Example 4 except the novel crystal form of fluoran (I) as isolated in Example 1 was replaced by the fluoran compound of formula (V). After calendering the heat sensitive recording paper showed a degree of soil to grey.

The heat sensitive paper rapidly developed a black colour by heating. After exposing the heat sensitive recording paper to 120 hrs of artificial daylight the uncoloured portion showed a high degree of soil to yellow. After storing at 60° C. and 50% relative humidity for 1 hr the uncoloured portion showed a high degree of soil to grey.

EXAMPLE 5

A heat sensitive recording paper was prepared by the process described in Example 4 except the novel crystal form of fluoran (I) as isolated in Example 1 was replaced by a 1:1 mixture of the novel crystal form of fluoran (I) and the commercial compound Pergascript Black T-2R (2-anilino-3-methyl-6-dibutylaminofluoran) available from Ciba Specialty Chemicals PLC. After calendering the heat sensitive recording paper showed a slight degree of soil to grey. The heat sensitive paper rapidly developed a black colour by heating. After exposing the heat sensitive recording paper to 120 hrs of artificial daylight the uncoloured portion showed virtually no soiling and retained high brightness. After storing at 60° C. and 50% relative humidity for 1 hr the uncoloured portion showed virtually no soiling and retained high brightness.

EXAMPLE 6

A heat sensitive recording paper was prepared by the process described in Example 4 except the novel crystal form of fluoran (I) as isolated in Example 1 was replaced by a 1:1 mixture of the novel crystal form of fluoran (I) and fluoran compound of formula (IV). After calendering the heat sensitive recording paper showed a degree of soil to grey. The heat sensitive paper rapidly developed a black colour by heating. After exposing the heat sensitive recording paper to 120 hrs of artificial daylight the uncoloured portion showed some soiling. After storing at 60° C. and 50% relative humidity for 1 hr the uncoloured portion showed virtually no soiling and retained high brightness.

EXAMPLE 7

A heat sensitive recording paper was prepared by the process described in Example 4 except the colour developer Bis phenol A was replaced with 4-hydroxy-4'-isopropoxydiphenylsulfone. After calendering the heat sensitive recording paper showed excellent background whiteness. The heat sensitive paper rapidly developed a black colour by heating. After exposing the heat sensitive recording paper to 120 hrs of artificial daylight the uncoloured portion showed virtually no soiling and retained high brightness. After storing at 60° C. and 50% relative humidity for 1 hr the uncoloured portion showed virtually no soiling and retained high brightness.

EXAMPLE 8

A heat sensitive recording paper was prepared by the process described in Example 4 except the colour developer Bis phenol A was replaced with 4,4' Bis phenol S.

After calendering the heat sensitive recording paper showed excellent background whiteness. The heat sensitive paper rapidly developed a black colour by heating. After exposing the heat sensitive recording paper to 120 hrs of artificial daylight the uncoloured portion showed virtually no soiling and retained high brightness.

EXAMPLE 9

A heat sensitive recording paper was prepared by the process described in Example 4 except the colour developer Bis phenol A was replaced with 4,4'-dihydroxy-3,3'-diallyldiphenyl sulfone. After calendering the heat sensitive recording paper showed excellent background whiteness. The heat sensitive paper rapidly developed a black colour by heating. After exposing the heat sensitive recording paper to 120 hrs of artificial daylight the uncoloured portion showed virtually no soiling and retained high brightness. After storing at 60° C. and 50% relative humidity for 1 hr the uncoloured portion showed virtually no soiling and retained high brightness.

What is claimed is:

1. A crystal form of a fluoran having the formula (I);

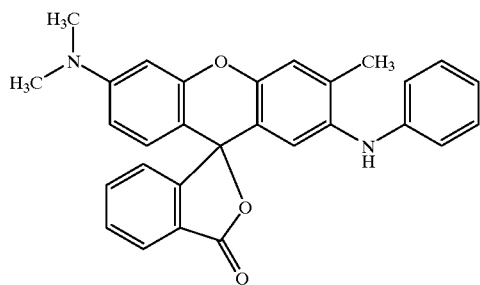

characterised by an X-ray powder diffraction diagram having high peaks at diffraction angles of 2θ 6.31, 12.37, 12.83, 17.02, 17.33, 18.10, 18.30.

2. The crystal form of claim 1 wherein the melting point is in the range 204–208° C.

3. A process for the preparation of the crystal form of the fluoran compound of claim 1 wherein the fluoran compound is obtained by carrying out a dehydrating condensation reaction of a compound having the formula (II):

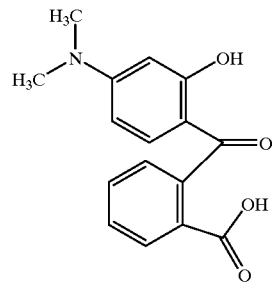

and a compound having formula (III):

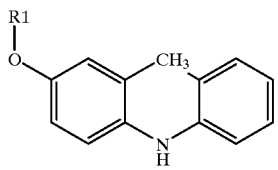

wherein R1 is Hydrogen or a lower alkyl group having 1–4 C atoms and the fluoran compound is isolated after a treatment with alkali in the presence of an organic solvent.

4. The process of claim 3 wherein the organic solvent is toluene.

5. The process of claim 3 wherein the crystalline fluoran compound may be further purified by recrystallisation from an organic solvent.

6. The process of claim 5 wherein the organic solvent is toluene.

7. The crystalline fluoran compound obtained by the process of claim 3.

8. The crystalline fluoran compound obtained by the process of claim 1.

9. A recording material comprising the crystal of the fluoran compound of claim 1 or claim 2.

10. A process for the preparation of a novel crystalline form of the fluoran compound having the formula (I)

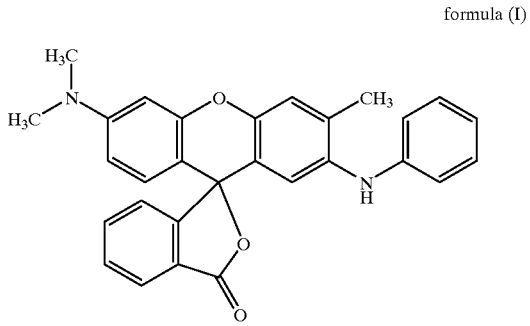

formula (I)

of claim 1 which comprises alkaline treatment in the presence of an organic solvent of the known lower melting fluoran compound having the formula (I).

11. A coating formulation for a thermally sensitive or pressure sensitive recording material which comprises:

(a) the fluoran compound according to claim 1;

(b) a developer;

(c) water and/or solvent; and optionally (d) a sensitizer.

12. A method of preparing a thermally sensitive or pressure sensitive recording material which comprises applying to a substrate an effective amount of the coating formulation of claim 11.

13. A method according to claim 12 wherein the recording material comprises paper.

14. A recording material according to claim 9 which comprises paper.

\* \* \* \* \*